United States Patent [19]

Goswami et al.

[11] Patent Number: 5,405,583
[45] Date of Patent: * Apr. 11, 1995

[54] SOLID STATE SENSOR FOR CARBON MONOXIDE

[75] Inventors: Kisholoy Goswami; Devinder P. S. Saini; Stanley M. Klainer, all of Henderson; Chuka H. Ejiofor, Las Vegas, all of Nev.

[73] Assignee: FCI - FiberChem, Inc., Las Vegas, Nev.

[ * ] Notice: The portion of the term of this patent subsequent to Apr. 12, 2011 has been disclaimed.

[21] Appl. No.: 22,140

[22] Filed: Feb. 25, 1993

Related U.S. Application Data

[63] Continuation-in-part of Ser. No. 9,066, Jan. 26, 1993, Pat. No. 5,302,350.

[51] Int. Cl.⁶ .................... G01N 31/00; G01N 33/00
[52] U.S. Cl. .................... 422/86; 422/82.05; 422/83; 436/134
[58] Field of Search ........... 422/83, 86, 98, 82.05; 436/134, 169; 502/400, 406; 356/345

[56] References Cited

U.S. PATENT DOCUMENTS

| | | | |
|---|---|---|---|
| 2,487,077 | 11/1949 | Shepherd | 436/134 |
| 4,043,934 | 8/1977 | Shuler et al. | 502/1 |
| 4,188,364 | 2/1980 | Gladden | 422/171 |
| 4,224,280 | 9/1980 | Takahama et al. | 422/98 |
| 4,441,981 | 4/1984 | Okamato et al. | 204/426 |
| 4,474,963 | 10/1984 | Gokel | 546/178 |
| 4,482,635 | 11/1984 | Herskovitz et al. | 436/134 |
| 4,668,635 | 5/1987 | Forster | 436/134 |
| 4,718,992 | 1/1988 | Funahashi et al. | 204/153.1 |
| 4,940,328 | 7/1990 | Hartman | 356/348 |
| 5,063,164 | 11/1991 | Goldstein | 436/169 |

FOREIGN PATENT DOCUMENTS

| | | |
|---|---|---|
| 295765 | 11/1991 | Germany . |
| 9105252 | 4/1991 | WIPO . |

OTHER PUBLICATIONS

Zumdahl, *Chemistry*, 1986, pp. 964–965.
Cosofret et al. "New neutral carrier based hydrogen . . . ." *J. Electroanal Chem.* 327(1–2), 137–46.
Tohda et al. "Miniature polymer matrix membrane . . . " *Bunseki Kagaku*, 39(11), 767–71.

*Primary Examiner*—Robert J. Warden
*Assistant Examiner*—Robert Carpenter
*Attorney, Agent, or Firm*—Henry P. Sartorio

[57] ABSTRACT

A solid state optical sensor for CO has a sensing material which includes a molybdenum, tungsten or vanadium color forming agent; a palladium, ruthenium or osmium catalyst; and an iron, chromium or cesium reversing agent. A redox property modifier and/or an interference suppressing agent may also be included. The chemistry is contained in a polymer embedding matrix, with permeation enhancer, if required. Solubility of the chemistry in the polymer matrix is enhanced by lipophilic counterions. The matrix with embedded sensing chemistry is coated on an optical substrate to form an optical transducer.

31 Claims, 6 Drawing Sheets

($R_1$, $R_2$, $R_3$, $R_4$ REPRESENT ALKYL CHAINS)

SOLID STATE SENSOR FOR CARBON MONOXIDE

RELATED APPLICATIONS

This invention is a continuation-in-part of application U.S. Ser. No 08/009,006, filed Jan. 26, 1993, now U.S. Pat. No. 5,302,350.

BACKGROUND OF THE INVENTION

This invention relates generally to chemical sensors for toxic gases, and in particular to carbon monoxide sensors.

Sensors and sensing systems for detecting toxic pollutants are gaining increasing prominence in process control, residential environment, transportation vehicles, and in work places. Carbon monoxide is an odorless poisonous gas, with an exposure limit of only 35 ppm.

Solid state sensing devices impart numerous advantages. In particular, solid state sensors are user friendly, possess extended shelf life and operational life, can be easily mass produced, and reduce the risk of improper handling by the user.

The prior art for detecting carbon monoxide colorimetrically involves the use of palladium and molybdenum compounds, as described by M. Shepherd, Anal. Chem. 19 (2), 77, (1947). The use of these compounds have also been reported as early as 1910 by C. Zenghelis, Z. Anal. Chem., 40, 429, (1910) and the literature was reviewed in 1935 by J. Schmidt, "Das Kohlenoxyd", Akad Verlag, Leipzig, P 186, (1935). This chemistry also appears in "Spot Tests in Inorganic Analysis" by F. Feigel, V. Anger, R. Oesper, Elsevier Publishing Company, New York, P. 168 (1972).

U.S. Pat. No. 3,112,999 to Grosskopf is directed to a solid state carbon dioxide sensing device.

The basic chemical reactions for the palladium catalyzed reduction of molybdenum by carbon monoxide are as follows:

$$Mo^{+6} + CO \rightarrow Mo^{+3} + CO_2 \quad (1)$$

$$Pd^{+2} + CO \rightarrow Pd^{0} + CO_2 \quad (2)$$

$$Pd^{0} + Mo^{+6} \rightarrow Pd^{+2} + Mo^{+3} \quad (3)$$

The reaction of carbon monoxide with molybdenum (Equation 1) is very sluggish. Therefore, palladium is employed as a catalyst, where palladium is first reduced by carbon monoxide. Reduced palladium, $Pd^0$, in turn then reduces the molybdenum to lower oxidation states the most common one being $Mo^{+3}$, which is also known as "molybdenum blue". Thus, a slightly yellow solution is changed to a blue color. The intensity of the blue color directly correlates to the extent of CO exposure. Unfortunately, however, the reduced molybdenum is rather stable, and does not quickly go back to the initial oxidation state so that the same chemistry could be recycled. This irreversibility makes this chemistry of limited use.

A reversible CO sensor is shown by Shuler et al, U.S. Pat. No. 4,043,934 which has a Mo, W or V color forming agent, Pd catalyst and Cu, Ni or Fe reversing agent. The sensing reagent is deposited on an inert carrier which is hydrophilic or contains water or OH groups, e.g. silica gel, alumina, polymeric alcohol, polyglycol, cellulose, glass wool and sponges.

M. K. Goldstein in U.S. Pat. No. 5,063,164 describes a biomimetic sensor for detecting the presence of airborne toxins including CO. That patent suggests several recipes for making regenerable sensors, but does not address the criteria or requirements for a successful reversible sensor; nor does it address the chemistry or mechanisms to make the CO sensor completely specific.

Goldstein shows a solid state CO sensor having five components: (1) palladium salt, (2) molybdenum and/or tungsten salt or acid salt, (3) copper salt, (4) cyclodextrin molecular encapsulant which encapsulates at least one but not all of the other components, and (5) chloride salt, all impregnated into a porous substrate. The Mo,W/Pd/Cu system is as in Shuler. The improvement is the encapsulant which extends sensor lifetime. An excess of chloride ions are also provided to extend lifetime. The substrates include silica-gel beads and porous glass, in which diffusion of gases can be rather slow.

Goldstein's patent does not reveal (a) how fast the reverse reaction occurs, or (b) whether it can stand a drastic environment like 100% CO. U.S. Pat. No. 5,063,164 uses $Cu^{2+}$ salts as the reversing agent. $Cu^{++}$ and $Cu^{+}$ ions are very stable at ambient atmospheric conditions. Therefore, the $Cu^{++}/Cu^{30}$ pair does not fully meet the criteria of a successful reversing agent for a deadly toxic gas like carbon monoxide.

SUMMARY OF THE INVENTION

Accordingly, it is an object to provide an improved optical sensor for carbon monoxide.

It is also an object to provide a solid state CO sensor.

It is another object to provide a solid state CO sensor which is reversible, eliminates interferences, and has an extended lifetime.

The invention is a solid state CO sensor which includes a color forming agent, a catalyst, and a reversing agent. The CO sensor can further include an interference suppressing agent, and a redox property modifier. The sensor can be formed with an improved embedding matrix, a gas permeation agent, and nonporous optical substrates. The preferred matrix is a polymer matrix. Solubility of inorganic salts in the polymer is improved by lipophilic counterion exchange.

DETAILED DESCRIPTION OF THE PREFERRED EMBODIMENTS

The invention is a solid state optical sensor for CO having a sensing material which includes a molybdenum, tungsten or vanadium color forming agent; a palladium, ruthenium or osmium catalyst; and an iron, chromium or cerium reversing agent. A redox property modifier and/or an interference suppressing agent may also be included. The chemistry is contained in a polymer embedding matrix, with permeation enhancer, if required. Solubility of inorganic ions in the polymer is increased by counterion exchange. The matrix with embedded sensing chemistry is coated on an optical substrate to form an optical transducer.

The color forming agent produces a measurable color change in the presence of CO. The catalyst speeds up the reaction. The reversing agent converts the color forming agent back to its original state for reuse. The redox property modifier extends the lifetime. The interference suppressing agent removes interfering species. The lipophilic counterion increases solubility of the sensing chemistry in the polymer embedding matrix.

Figure 1:
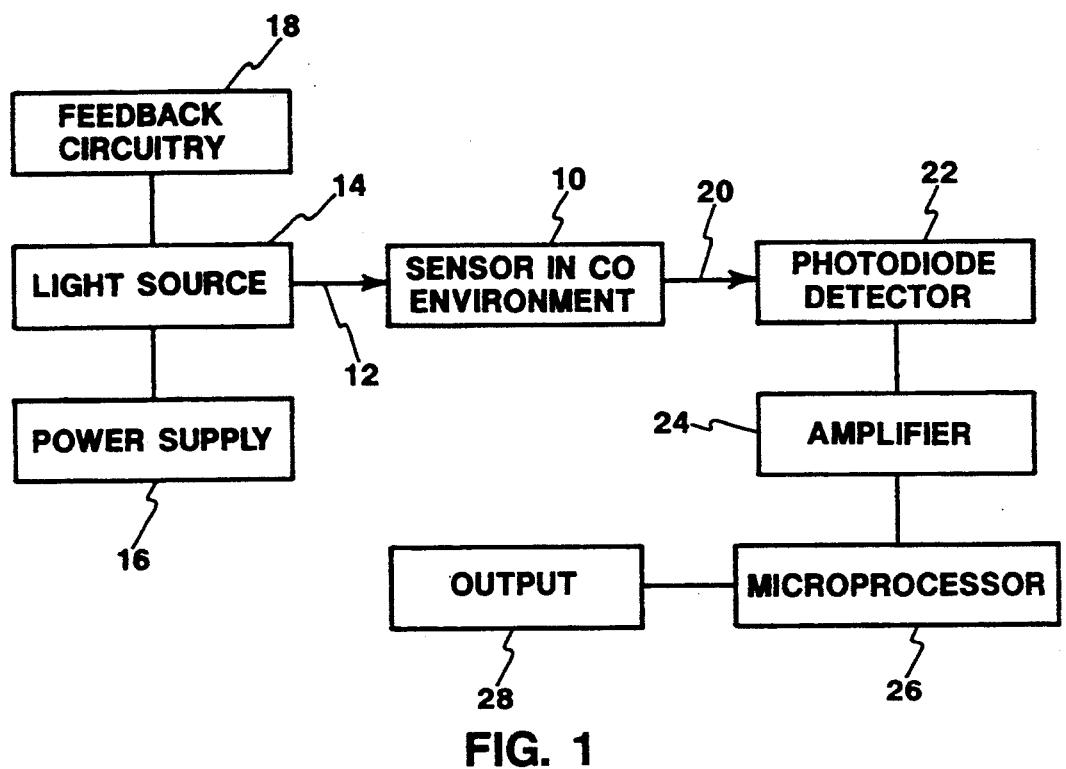
FIG. 1 is a schematic view of a solid state CO sensor measurement system.

As shown in FIG. 1, a solid state CO sensor 10 is placed in a measuring environment. A light signal 12 from source 14 is input into sensor 10. Source 14 is powered by supply 16 and is controlled by feedback circuit 18, if required. Sensor 10 is an optical transducer whose output signal 20 varies as a function of CO exposure, for a given input signal 12. Output signal 20 is detected by detector 22, whose output is connected through amplifier 24 to microprocessor 26 which is connected to output means 28.

The sensor can be a hybrid device, or it can be an integrated optic chemical sensor. An incandescent lamp, laser, laser diode or light emitting diode will be employed as the source, while a photodiode, CCD or an interferometer will be employed at the detection end. The device would be used for detecting the instantaneous level of a toxic pollutant as well as for detecting a cumulative amount for a predetermined period of time. The device will make both kinetic and equilibrium measurements.

The general working principle of the solid state CO sensor is based on the attenuation of a transmitted light beam during its interaction with the sensing material at a time when the sensing material is exposed to the analyte (CO). The attenuation of light depends on the concentration of the analyte, as well as on the exposure time. This attenuation can occur because of (a) attenuated total internal reflection (ATR) (FIG. 2A), (b) absorption (FIG. 2B), or (c) both.

Figure 2A:
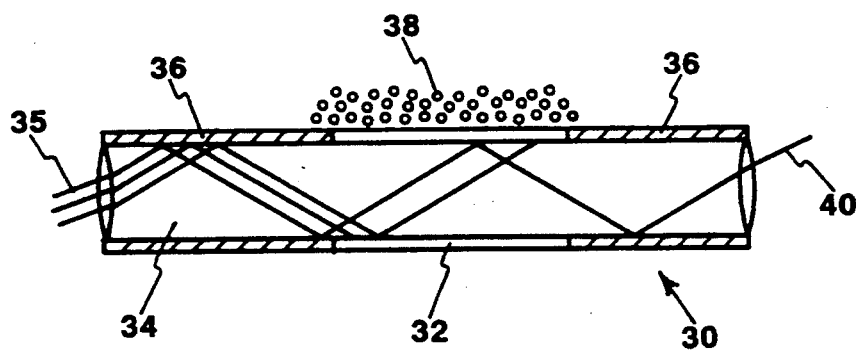
FIGS. 2A,2B,2C illustrate ATR and absorption solid state CO sensors.

As shown in FIG. 2A, ATR sensor 30 has a sensor coating 32 formed on a portion of optical fiber core 34. Sensor coating 32 includes the CO sensitive sensing chemistry in a suitable CO permeable solid state matrix. An input light beam 35 travels down the fiber optic core 34 by total internal reflection at the interface with clad 36. When sensor coating 32 is exposed to CO environment 38, coating 32 changes color, which attenuates the incident light beam 35 which is totally internally reflected from the region of core 34 covered by coating 32. An attenuated light beam 40 is output from sensor 30. Thus, sensor 30 is an ATR optical transducer, where the attenuation provides a measure of the CO environment.

Figure 2B:
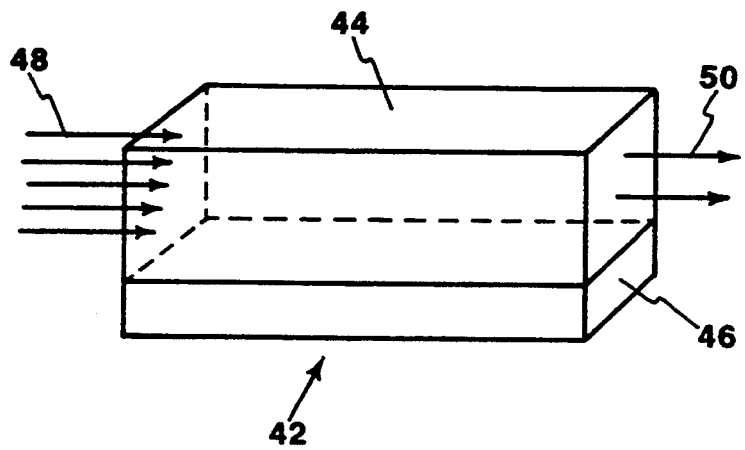

As shown in FIG. 2B, absorption sensor 42 is formed of a strip or block 44 which is made of the CO sensitive sensing chemistry in a suitable CO permeable solid state matrix. Strip or block 44 can be mounted on a suitable support substrate 46. Incident light beam 48 passes straight through strip or block 44. Changes in color (absorption) caused by CO exposure produce an attenuated output beam 50. Instead of passing beam 48 through block/strip 44 parallel to substrate 46, the beam may pass through substrate 46 if the substrate 46 is transparent. Thus sensor 42 is an absorption type optical transducer, where transmitted beam attenuation provides a measure of the CO environment.

In order to succeed commercially, the sensor has to be fast responding and reversible with a reproducible response. The sensor should be specific and it should have extended lifetime. Its production should be relatively easy.

According to the invention, the following classes of materials are employed for building the sensor:

[A] Color forming agent: (1) Compounds of molybdenum, tungsten or vanadium including but not limited to ammonium molybdophosphate, molybdosilicic acid and salts thereof, molybdophosphoric acid, ammonium molybdate, tungstosilicic acid and salts thereof, molybdenum trioxide, tungsten trioxide, tungstophosphoric acid, ammonium tungstate, organomolybdenum or organotungsten compounds, heteropolyacids of tungsten and molybdenum, alkali metal or alkaline earth metal salts of the tungstate and molybdate anions, vanadium (V) oxide, vanadyl phthalocyanine, vanadium (V) trichloride oxide, vanadium (V) trifluoride oxide, vanadium triisopropoxy oxide, vanadyl octaethylporphine; (2) any other organic compound or transition metal complex, e.g., hemoglobin or its analogs, that shows color change directly with CO or with reduced palladium, ruthenium or osmium.

[B] Catalyst: (1) Palladium (II) compounds including but not limited to palladium chloride, palladium acetate, palladium sulfate, palladium sulfite, palladium oxalate, palladium citrate, palladium pyrosulfite, palladium bromide, palladium perchlorate, palladium iodide, $CaPdCl_4$, $Na_2PdCl_4$, $K_2PdCl_4$, palladium acetylacetonate, allylpalladium bromide; (2) Ruthenium (VIII) compounds including but not limited to ruthenium (VIII) oxide; (3) Osmium (VIII) compounds including but not limited to osmium (VIII) oxide; (4) Any other inorganic compound with multiple stable oxidation states having redox properties compatible to reduction by CO in the presence or absence of a modifier.

[C] Reversing Agents: (1) Ferric(III) salts including but not limited to ferric chloride, ferric sulfate, ferric bromide, ferric iodide, ferric perchlorate, ferric fluoride, ferric acetylacetonate, ferric ammonium citrate, ferric ammonium sulfate, ferric nitrate, ferric oxalate, ferric phosphate, ammonium ferric citrate, ammonium ferric oxalate; (2) Chromium (VI) salts including but not limited to potassium dichromate, ammonium dichromate, sodium dichromate, sodium chromate, potassium chromate; (3) Cerium (IV) salts including but not limited to cerium sulfate, ammonium cerium nitrate, ammonium cerium sulfate; (4) Any other organic compound or transition metal complex or inorganic compound capable of reverting the color reaction and itself being regenerable at ambient conditions.

[D] Redox property modifier: (1) Salts of acetic acid, including but not limited to sodium acetate, potassium acetate, magnesium acetate, copper acetate, ammonium acetate, lithium acetate; or (2) Any other compound that prevents the color forming reaction in the absence of CO.

[E] Interference suppressing agent: Sodium, potassium, calcium, ammonium, lithium, beryllium, magnesium, aluminum, platinum, cobalt salts with counterions including but not limited to nitrate, acetate, chloride, sulfate, phosphate, chlorate, perchlorate, nitrite, carbonate, bicarbonate. This group includes ions forming a colorless or white precipitate with the interfering material or a precipitate which has a color which either does not overlap in the measurement window of wavelengths or has an overlap which is resolvable by applying smart computer software, for example, chemometrics.

[F] Embedding Matrix: Film forming crosslinkable/polymerizable monomer and polymer, including but not limited to poly (vinyl chloride) (PVC), carboxylated PVC, polystyrene, cellulose derivatives, variations of plexiglass, silanes, siloxanes, silicones. The matrix could also be formed of gel-forming material, such as sol gel, silica gel, or hydrogel. The matrix should not have functionalities, e.g., $OH^{31}$, which reduce the color forming agent or catalyst.

[G] Permeation enhancer: Plasticizer, including but not limited to tributyl phosphate, sebacic acid dibutyl ester, dioctyl phthalate.

[H] Transducer/support substrate: Supporting structure for matrix with embedded chemistry, including but not limited to planar waveguide, optical fiber, slab, disc, prism, strips, rod, pipe, cube, film. The substrate materials include both amorphous and single-crystal or polycrystalline materials, inorganic and organic compounds, and even some liquids, for example, liquid crystals. Types of glass include quartz, pyrex, sodalime, phosphate, borosilicate, fluoride, chalcogenide, fluorozirconate. The substrate can be integrated optic materials including but not limited to oxides, nitrides, sulfides, oxynitrides, zirconates, titanates. Polymers and organic materials can be pure or doped, including but not limited to plexiglass and polyimide. Single crystal materials include but are not limited to silicon, lithium niobate, lithium tantalate, barium tellurate, and garnets. Semiconductor materials can also be employed as a substrate. The sensing chemistry/matrix is deposited on the substrate by evaporation, lamination, spraying, dip-coating, casting and spreading, Q-tipping, spin-coating, etc.

Figure 2C:
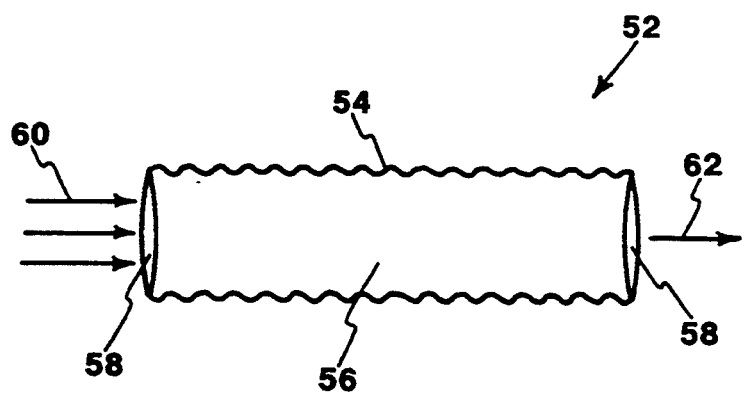

The substrate can be an operational part of the optical transducer as in FIG. 2A, or merely a support as in FIG. 2B. The substrate can also take the form of containment means, as shown in FIG. 2C. Sensor 52 is formed of a gas permeable tubular membrane 54 filled with a jelled sensing chemistry matrix 56. Optical windows 58 are placed at the ends of tube 54 to pass input light beam 60 and output beam 62.

The present invention is based on the judicial choice of one component from each category. In a preferred embodiment of the chemical sensor for carbon monoxide, molybdosilicic acid is the color forming agent; palladium sulfate is the catalyst; anhydrous ferric chloride is the reversing agent; sodium acetate is both the redox property modifier, and suppressor of hydrogen sulfide interference; PVC is the embedding matrix, while tributyl phosphate is the CO permeation enhancer. Finally, the sensing cocktail is coated on an optical fiber with a Q-tip.

A typical formulation is described as follows:
1. Weigh 0.012 g Palladium sulfate.
2. Add 3 drops of freshly prepared 10% $Na(OAc)_2$.
3. Mix thoroughly.
4. Add 0.048 g molybdosilicic acid and mix well.
5. Add 6 ml of 10% PVC in tetrahydrofuran, and mix thoroughly.
6. Add 24 drops of tributyl phosphate, and mix well.
7. Add 0.024 g of ferric chloride, and mix well.
8. Cast a portion of this batch of sensing chemistry/matrix on a glass slide for quality control; check using a uv/vis spectrophotometer.
9. Coat optical fibers with Q-tip.

Figure 3:
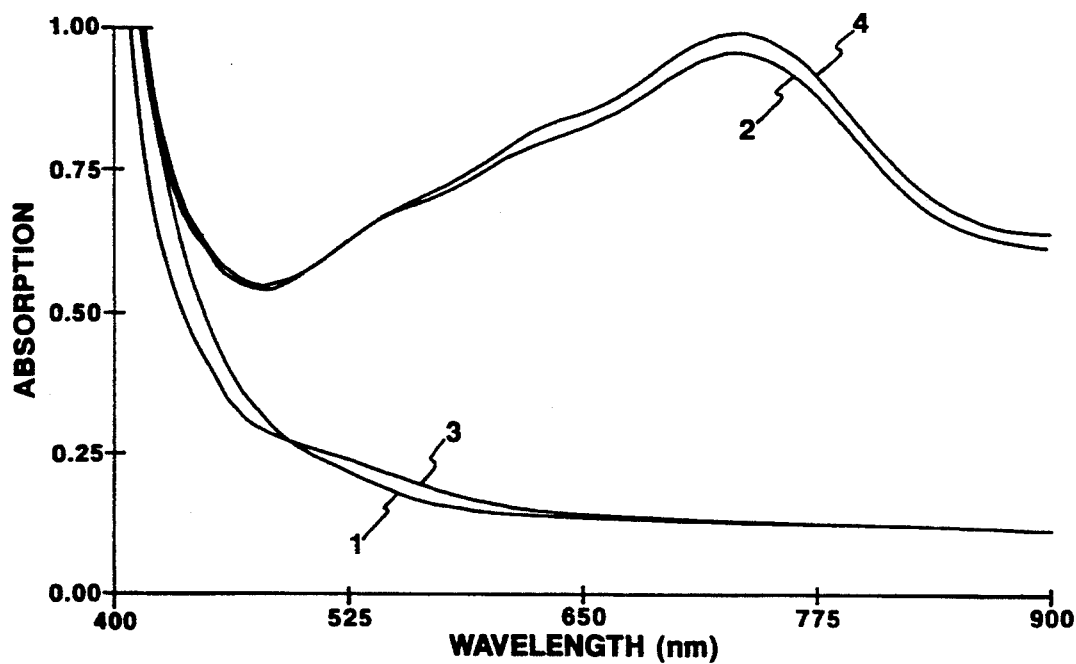
FIG. 3 is the absorption spectrum of the CO sensing chemistry.
Figure 4:
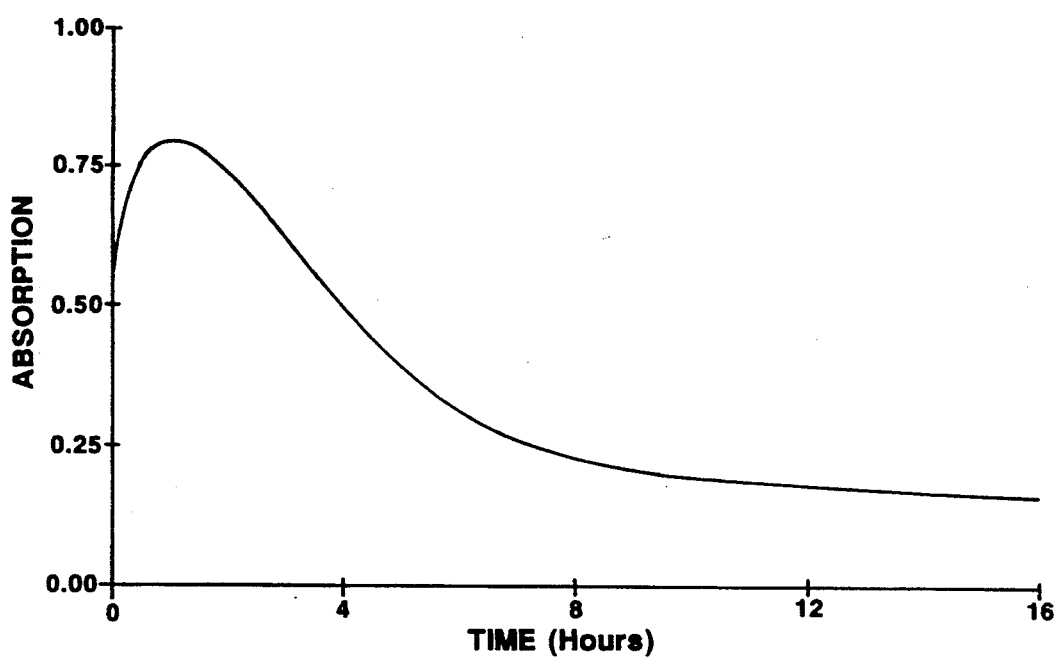
FIG. 4 shows the recovery time of the CO sensing chemistry.

FIG. 3 shows the performance (absorption spectra) of the sensing chemistry as determined by uv/vis. The chemistry is used on a glass slide, and the coating thickness is about 50 microns. Because of this very small path length, the glass slide is exposed to 100% CO. Curve 1 is the background before exposing the chemistry to 100% CO, Curve 2 is the spectrum after exposure of the chemistry to 100% CO for 30 minutes, Curve 3 is the spectrum taken after the sensing chemistry has reverted, and Curve 4 is the absorption spectrum taken after the chemistry was re-exposed to 100% CO. As FIG. 3 shows, the interaction of CO with the chemistry produces a broad absorption spectrum. FIG. 3 also shows the reproducibility of the sensor response. FIG. 4 shows how quickly the chemistry reverts back to the starting stage.

It is difficult to dissolve inorganic salts in an organic matrix The small ion-counterion pairs, e g., $Pd^{+2}$, $SO_4^{-2}$, behave as point charges and are expelled by the organic matrix. Thus it is necessary to improve the solubility in a polymer matrix of the inorganic salts which provide the color forming agent, catalyst and reversing agent in order to form a solid state CO sensor with fast response, high sensitivity and fast regeneration. According to the invention, the solubility of the inorganic salts in a polymer matrix is improved by counterion exchange with lipophilic counterions. The lipophilic counterions are counterions with hydrophobic chains which go easily into organic media. Thus, the sulfate counterion can be exchanged with a pair of dodecylsulfate counterions, which contain a $C_{12}$ chain.

Figure 6A:
FIGS. 6A–D illustrate various ions with lipophilic counterions.
Figure 6B:
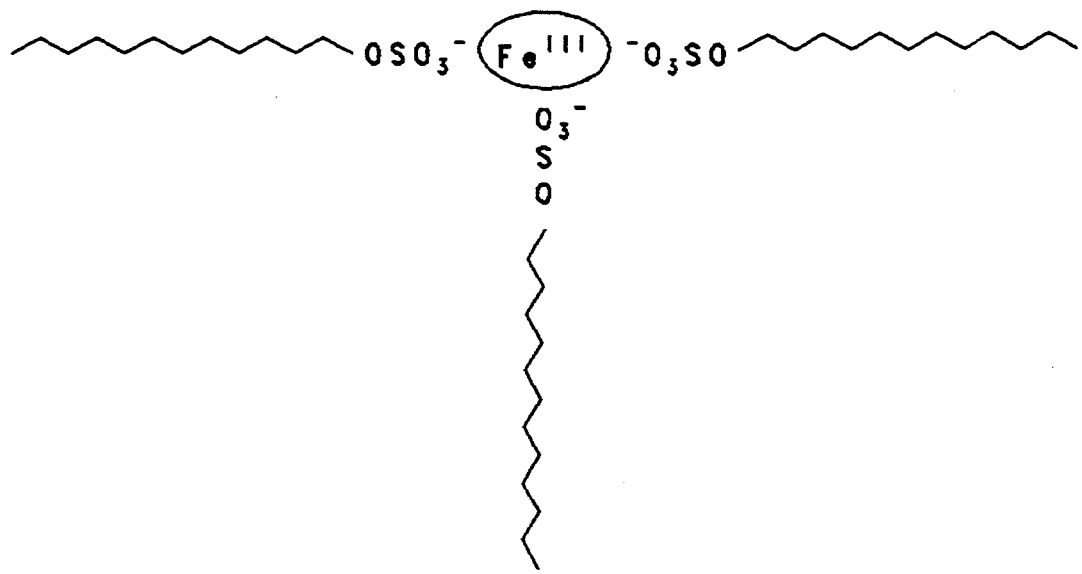
Figure 6C:
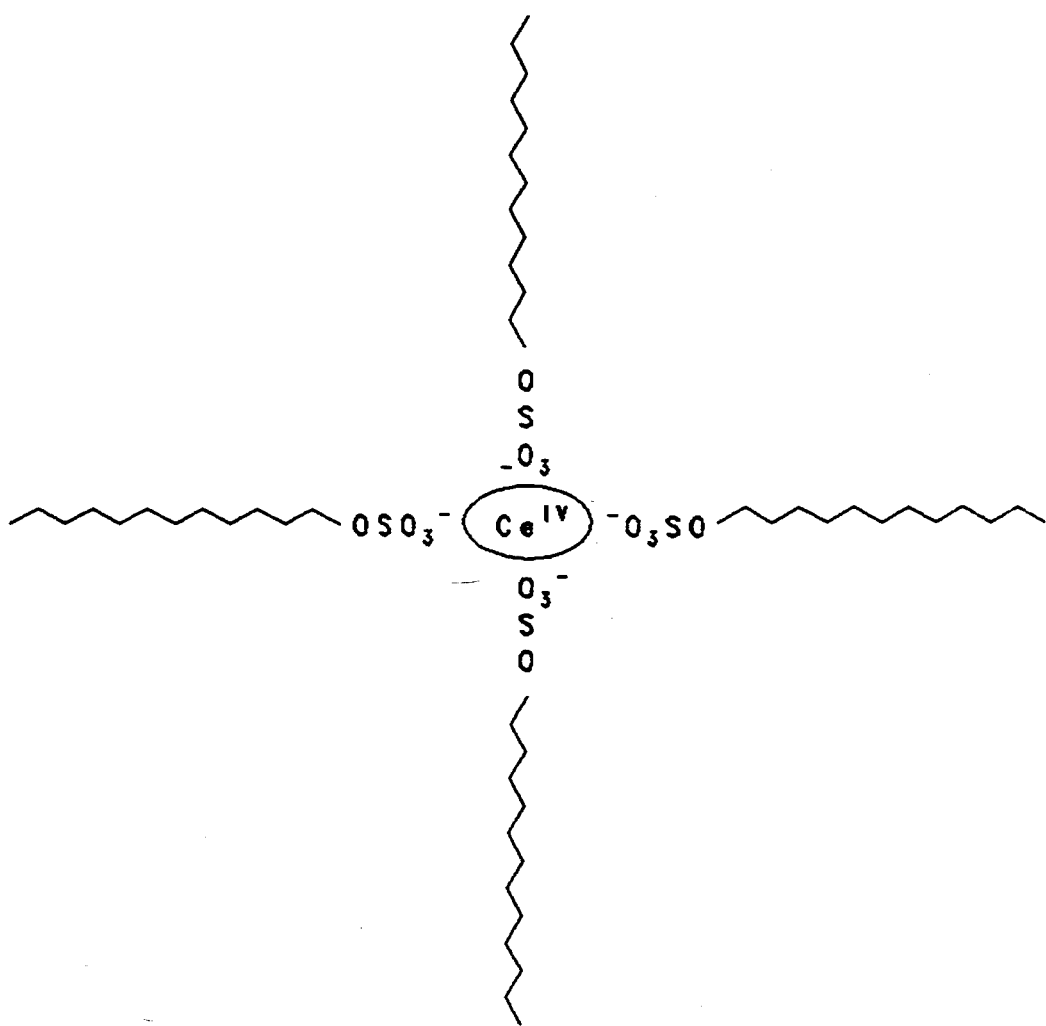
Figure 6D:
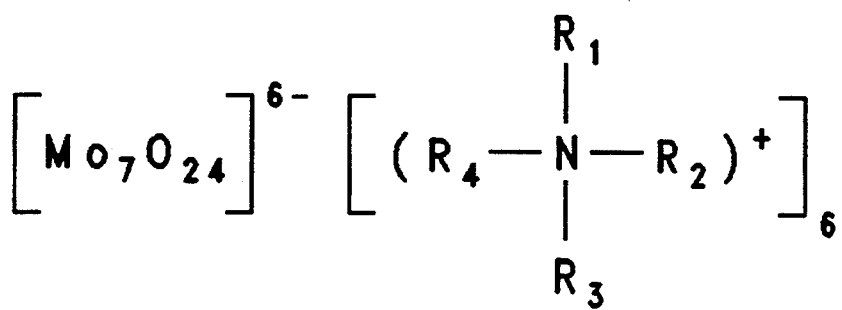

The exchange process can be readily carried out. The palladium sulfate salt is placed in a solution. The dodecylsulfate surfactant is added to the solution. The palladium dodecylsulfate is extracted from the solution with non-polar organic solvents, and later recovered by evaporating the solvent. The palladium dodecylsulfate salt is then used to prepare the CO sensing chemistry. Similarly, lipophilic counterions can be added to the reversing agent or to the color forming agent. FIGS. 6A-C show the Pd(II), Fe(III) and Ce(IV) ions with dodecylsulfate counterions. FIG. 6D shows a molybdenum oxide anion with hydrophobic quaternary ammonium cations, i.e., nitrogen with four long hydrophilic chains attached, e.g., groups $R_{1-4}$ represent alkyl chains. The large organic counterions facilitate solubility of the ions in the polymer.

Figure 5:
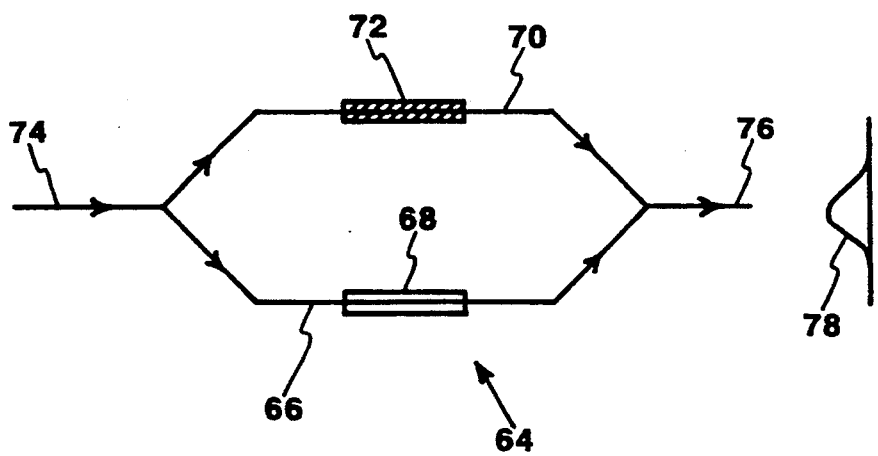
FIG. 5 is a schematic view of an interferometric measurement CO sensor.

A number of techniques can be applied for measuring CO. For example CO can be quantified by measuring the intensity of a band of wavelengths. The intensity modulation can arise from either attenuated total internal reflection phenomenon, or from a straight-through absorption process, as shown in FIGS. 2a, and 2b. Alternatively, as FIG. 5 shows, carbon monoxide can be quantified from phase modulation or interferometric measurements.

The interferometric sensor 64 (Mach-Zehnder configuration) has two arms, a sensing arm 66 containing sensing chemistry/matrix 68, and a reference arm 70 containing sensing chemistry/matrix 72. Sensing arm 66 is exposed to CO while reference arm 70 is not. An input light beam 74 having a well defined mode is split and input into arms 66, 70. As sensing chemistry 68 reacts with CO, it changes the mode propagation characteristics of arm 66 so that the portion of light beam that traverses arm 66 will change its mode while the portion that traverses arm 70 will not. The outputs of arms 66, 70 are recombined to produce output beam 76. Because of the differences in modes caused by CO exposure, output beam 76 will exhibit an interference pattern 78. An interferometric sensor can also be implemented in a single waveguide channel by propagating a light beam having two modes, one of which is affected by the change in absorbance of the sensing chemistry on the waveguide. The change in interference pattern between the two modes is a measure of the CO exposure.

Changes and modifications in the specifically described embodiments can be carried out without departing from the scope of the invention which is intended to be limited only by the scope of the appended claims.

We claim:

1. A solid state CO sensor comprising:
    a CO sensing chemistry, comprising:
        a color forming agent comprising a source of $Mo^{+6}$, $W^{+6}$ or $V^{+5}$ ions;
        a catalyst comprising a source of $Pd^{+2}$, $Ru^{+8}$ or $Os^{+8}$ ions;
        a reversing agent comprising a source of $Fe^{+3}$, $Cr^{+6}$ or $Ce^{+4}$ ions;
        a redox property modifier comprising a source of acetate ions;
        a polymer embedding matrix containing the CO sensing chemistry.

2. The CO sensor of claim 1 further comprising a light source for inputting a light beam into the matrix with embedded chemistry and a detector for measuring an attenuated light beam from the matrix with embedded chemistry.

3. The CO sensor of claim 1 wherein polymer is selected from the group consisting of poly(vinyl chloride) (PVC), carboxylated PVC, polystyrene, cellulose derivatives, variations of plexiglass, silanes, siloxanes, silicones.

4. The CO sensor of claim 1 wherein at least one of the color forming agent, catalyst or reversing agent comprise an active ion with a lipophilic counterion.

5. The CO sensor of claim 1 further comprising a permeation enhancer in the matrix.

6. The CO sensor of claim 5 wherein the permeation enhancer is a plasticizer.

7. The CO sensor of claim 1 wherein the source of $Mo^{+6}$ ions is a molybdenum salt or acid salt or organometal complex;
    the source of $W^{+6}$ ions is a tungsten salt or acid salt or organometal complex;
    the source of $V^{+5}$ ions is a vanadium salt or organometal complex;
    the source of $Pd^{+2}$ ions is a palladium salt;
    the source of $Ru^{+8}$ ions is a ruthenium salt;
    the source of $Os^{+8}$ ions is an osmium salt;
    the source of $Fe^{+3}$ ions is an iron salt;
    the source of $Cr^{+6}$ ions is a chromium salt;
    the source of $Ce^{+4}$ ions is a cerium salt.

8. The CO sensor of claim 7 wherein the molybdenum salt or acid salt is selected from the group consisting of molybdosilicic acid and salts thereof, molybdenum trioxide, heteropolyacids of molybdenum, ammonium molybdate, ammonium molybdophosphate, molybdophosphoric acid, organomolybdenum compounds, and alkali metal or alkaline earth metal salts of the molybdate anion;
    the tungsten salt or acid salt is selected from the group consisting of tungstosilicic acid and salts thereof, tungstophosphoric acid, organotungsten compounds, heteropolyacids of tungsten, tungsten trioxide, ammonium tungstate, and alkali metal or alkaline earth metal salts of the tungstate ion;
    the vanadium salt or organometal complex is selected from the group consisting of vanadium (V) oxide, vanadyl phthalocyanine, vanadium (V) trichloride oxide, vanadium (V) trifluoride oxide, vanadium triisopropoxy oxide, vanadyl octaethylporphine;
    the palladium salt is selected from the group consisting of palladium sulfate, palladium sulfite, palladium pyrosulfite, palladium chloride, palladium bromide, palladium acetate, palladium perchlorate, $CaPdCl_4$, $Na_2PdCl_4$, $K_2PdCl_4$, palladium oxalate, palladium citrate, palladium acetylacetonate, allylpalladium bromide;
    the iron salt is selected from the group consisting of ferric chloride, ferric sulfate, ferric bromide, ferric iodide, and ferric perchlorate, ferric fluoride, ferric acetylacetonate, ferric ammonium citrate, ferric ammonium sulfate, ferric nitrate, ferric oxalate, ferric phosphate, ammonium ferric citrate, ammonium ferric oxalate;
    the chromium salt is selected from the group consisting of potassium dichromate, ammonium dichromate, sodium dichromate, sodium chromate, potassium chromate;
    the cerium salt is selected from the group consisting of cerium sulfate, ammonium cerium nitrate, ammonium cerium sulfate.

9. The CO sensor of claim 1 wherein the redox property modifier is an acetic acid salt.

10. The CO sensor of claim 9 wherein the acetic acid salt is selected from the group consisting of sodium acetate, potassium acetate, magnesium acetate, copper acetate, ammonium acetate, lithium acetate.

11. The CO sensor of claim 1 wherein the CO sensing chemistry further comprises an interference suppressing agent.

12. The CO sensor of claim 1 wherein the interference suppressing agent comprises a source of ions which form a colorless or white precipitate with an interfering species.

13. The CO sensor of claim 12 wherein the interference suppressing agent is selected from the group consisting of sodium, potassium, calcium, ammonium, lithium, beryllium, magnesium, calcium salts with counterions selected from nitrate, acetate, chloride, sulfate, phosphate, chlorate, nitrite, carbonate, bicarbonate.

14. The CO sensor of claim 11 wherein the interference suppressing agent comprises a source of ions which form, with an interfering species, a precipitate which has a color which does not overlap a measurement window of wavelengths.

15. The CO sensor of claim 11 wherein the interference suppressing agent comprises a source of ions which form, with an interfering species, a precipitate which has a color which has a resolvable overlap with a measurement window of wavelengths.

16. The CO sensor of claim 1 further comprising a substrate on which the matrix with embedded chemistry is deposited.

17. The CO sensor of claim 16 wherein the substrate is a support structure on which the matrix with embedded chemistry is mounted.

18. The CO sensor of claim 16 wherein the substrate is an optical structure through which a light beam is transmitted to and from the matrix with embedded chemistry.

19. The CO sensor of claim 18 wherein the optical structure is a planar or fiber optic waveguide.

20. The solid state sensor of claim 18 wherein the optical structure is a waveguide, and further comprising a source of an input light beam having two interfering modes, one of which is changed by changing absorption caused by a color change of the embedded chemistry.

21. The solid state sensor of claim 18 wherein the optical structure comprises a Mach-Zehnder interferometer having, a sensing arm and a reference arm, each having the matrix with sensing chemistry formed thereon, wherein the sensing arm is exposed to a sample while the reference arm is not, wherein the mode of a light beam transmitted through the sensing arm is changed by changing absorption caused by a color change of the embedded chemistry and interferes with a light beam transmitted through the reference arm.

22. In a solid state CO sensor having a color forming agent, a catalyst, and a reversing agent embedded in a porous matrix, the improvement comprising at least one of:
  selecting the catalyst from $Ru^{+8}$ or $Os^{+8}$ ions;
  selecting the reversing agent from $Cr^{+6}$ or $Ce^{+4}$ ions.

23. A solid state CO sensor comprising:
  a CO sensing chemistry, comprising:
    a color forming agent selected from molybdenum tungsten or vanadium;
    a catalyst selected from palladium ruthenium or osmium;
    a reversing agent selected from iron, chromium, cerium or nickel;
    a redox property modifying agent which is an acetate;
    an interference suppressing agent;
    an embedding matrix containing the CO sensing chemistry.

24. The CO sensor of claim 23 wherein the embedding matrix comprises a polymer or cross linkable and/or polymerizable monomer.

25. The CO sensor of claim 24 wherein the sensing chemistry further comprises lipophilic counterions.

26. The CO sensor of claim 23 wherein the embedding matrix comprises a gel forming material.

27. The CO sensor of claim 26 wherein the gel forming material is selected from the group consisting of sol gel, silica gel and hydrogel.

28. The CO sensor of claim 23 wherein the redox property modifier is an acetic acid salt.

29. The CO sensor of claim 20 wherein the acetic acid salt is selected from the group consisting of sodium acetate, potassium acetate, magnesium acetate, copper acetate, ammonium acetate, lithium acetate.

30. The CO sensor of claim 23 wherein the interference suppressing agent comprises a source of ions which form a colorless or white precipitate with an interfering species.

31. The CO sensor of claim 30 wherein the interference suppressing agent is selected from the group consisting of sodium, potassium, calcium, ammonium, lithium, beryllium, magnesium, calcium salts with counterions selected from nitrate, acetate, chloride, sulfate, phosphate, chlorate, nitrite, carbonate, bicarbonate.

* * * * *